United States Patent [19]
Marshall, Sr.

[11] Patent Number: 5,242,388
[45] Date of Patent: Sep. 7, 1993

[54] INOCULATION SYSTEM

[75] Inventor: William M. Marshall, Sr., Salem, Va.

[73] Assignee: Morf, Inc., Salem, Va.

[21] Appl. No.: 822,642

[22] Filed: Jan. 21, 1992

[51] Int. Cl.$^5$ .............................................. A61B 17/20
[52] U.S. Cl. ........................................ 604/47; 604/73; 604/131; 119/6.8; 119/713
[58] Field of Search .................. 604/46, 47, 51, 73, 604/131; 606/117; 119/6.8, 97.1, 174

[56] References Cited

U.S. PATENT DOCUMENTS

| | | | |
|---|---|---|---|
| 2,575,648 | 11/1951 | Willson | 604/47 |
| 2,617,418 | 11/1952 | Del Pico | 604/47 |
| 2,952,257 | 9/1960 | Rubery . | |
| 3,774,578 | 11/1973 | Randolph et al. . | |
| 4,453,926 | 6/1984 | Galy | 604/47 |
| 4,711,247 | 12/1987 | Fishman | 604/47 X |
| 4,990,135 | 2/1991 | Truesdale, Jr. | 604/47 |
| 5,104,620 | 4/1992 | Wiley et al. | 604/47 X |

*Primary Examiner*—Randall L. Green
*Assistant Examiner*—Mary Beth O. Jones
*Attorney, Agent, or Firm*—John F. C. Glenn

[57] ABSTRACT

Apparatus for operating needle to inoculate the web of a bird's wing. An arm rocks a needle holder back and forth between a serum container and web positioner, along a path which causes the needle holder to move substantially vertically into and out of the container and web positioner. Gears cause the needle holder to pivot on the arm in response to pivotal movement of the arm, so that the needle points downwardly throughout its movement.

13 Claims, 3 Drawing Sheets

INOCULATION SYSTEM

FIELD OF THE INVENTION

This invention relates to inoculators for birds, particularly poultry.

BACKGROUND OF THE INVENTION

It is currently customary to inoculate poultry with serum for fowl pox by having one person hold a chicken while another person injects the serum by passing a needle, or pair of needles, coated with the serum through the web of a wing. Efforts have been made to improve the reliability of this procedure, and to reduce the time and manpower required, as shown, for example, in U.S. Pat. No. 2,952,257 of Sep. 13, 1960 (Rubery). The patent discloses a foot pedal operable to plunge a needle downwardly through the web of a wing into a bottle of serum, where some of the serum adheres to the side of the needle, and then to pull the needle upwardly in order to deposit some of the adhering serum. This makes it possible for one person to hold and inoculate a bird, but the disclosed apparatus has some problems. For example, the operator cannot see the part of the needle extending beneath the web, and consequently is ignorant of whether the needle may have gone through a feather beneath the web so that the serum picked up from the supply below will be wiped off by the feather before it reaches the web. For whatever reason, the Rubery apparatus has not displaced hand held needles for inoculating poultry.

SUMMARY OF THE INVENTION

In accordance with the invention, one or more inoculating needles are mechanically operated to perform a sequence of operations. The final operation leaves the needles (preferably a pair), supplied with serum and pointed down toward the place where the web of a bird's wing can be positioned by means which predetermine the position of the web and also serve as a guard to protect the fingers of the person inoculating the bird. When the operating sequence starts, the needles first move down to pierce a web beneath them, leaving the pre-applied serum in the web as the needles pass through it. The needles then retract upwardly and, while retaining their substantially vertical alignment, move away from the web positioning means to a container holding a supply of the serum; are then dipped downwardly in to the serum supply, and then raised out of it and transferred back to the final position described above. The web can be withdrawn as soon as the needle has retracted after injection, without waiting for the completion of the rest of the sequence. The fingers of a person operating the equipment are protected from accidental contact with the needles by the guard means during the period while the person's fingers are needed to hold the web near the needles, and are protected from the needles when they are transferred to and from the serum supply by locating the supply away from the place where the web is held for inoculation.

In the preferred practice of the invention the needles are carried on a mount which swings them in an arc extending in a half circle between the position of the needles at the end of their downward movement through the web to their position at the end of their downward movement into the reservoir of serum. To accomplish this swing, the motor driving the equipment preferably turns a crank arm to cause reciprocation while a member acting as a rack turns a gear back and forth which is connected to the swing arm carrying the needle holder. The needle holder is pivoted on the swing arm and is held upright during the operation.

The means for holding the needle holding unit with the needles extending downwardly during the sequence of operations preferably comprises a pair of gears at opposite ends of the swing arm and a flexible belt trained around the gears and having teeth along its inner periphery meshing with the gears. The gear at the inner end of the swing arm is fixed relative to the apparatus base, and the gear at the outer end of the swing arm is keyed to a shaft which is journaled in the outer end of the swing arm and is fixed to the mounting means for the needles.

The starting switch for the motor is operable by a button easily pressed by the person holding the wing web in position to be pierced by the needles, and a stopping switch is automatically operated when the swing arm reaches a predetermined position to hold the needles ready for the next sequence of operations. The stopping switch not only cuts off power to the motor but also activates a brake to prevent further rotation of the motor due to inertia. This insures that at the end of the sequence the needles will be positioned properly for the beginning of the next sequence.

Other details, objects and advantages of the invention will be become apparent as the following disclosure of the illustrated embodiment proceeds.

DESCRIPTION OF THE DRAWINGS

A present preferred embodiment of the invention is illustrated in the following drawings, in which.

DETAILED DESCRIPTION OF THE ILLUSTRATED EMBODIMENT

Figure 1:
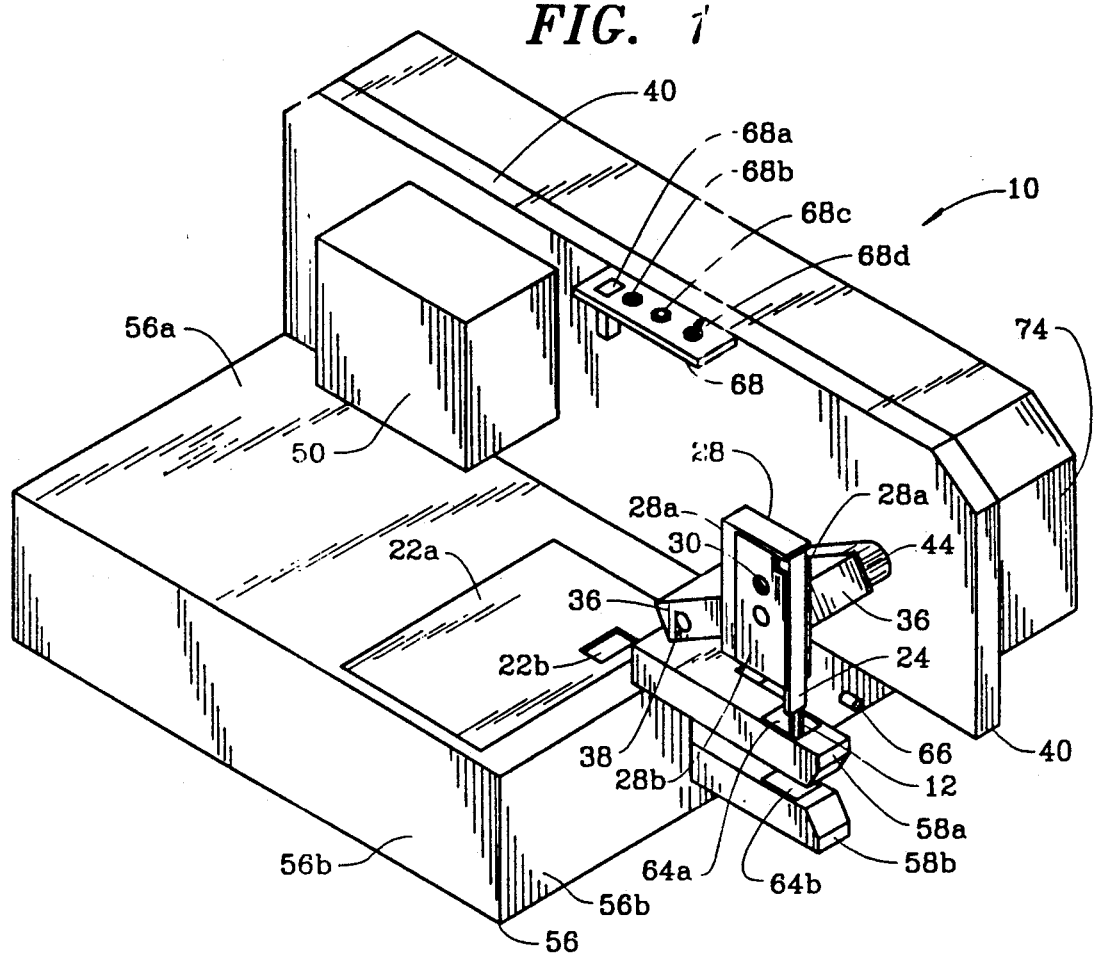
FIG. 1 shows a schematic isometric front view of apparatus for chicken inoculation.
Figure 2:
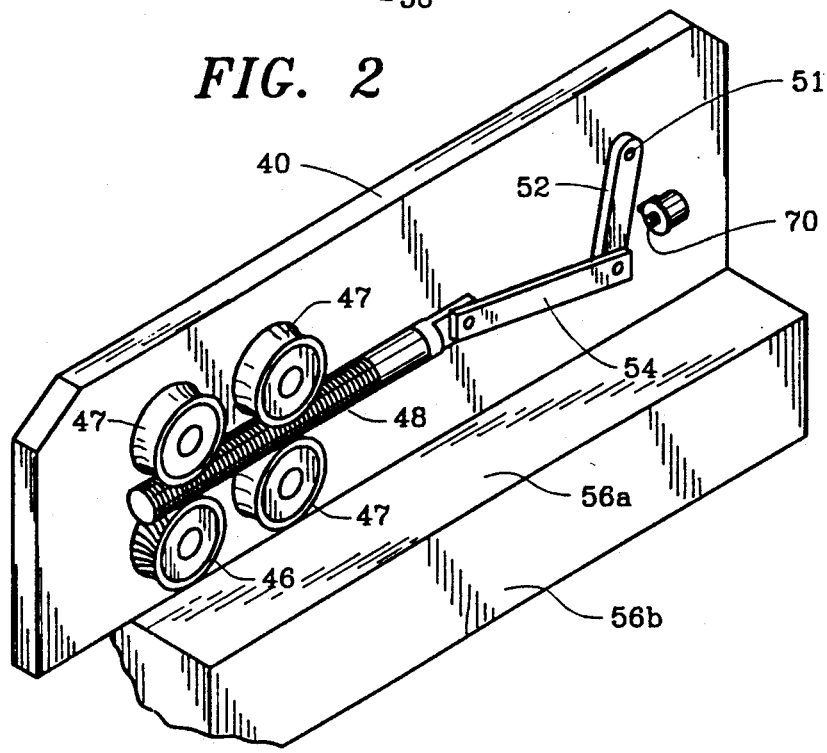
FIG. 2 shows a schematic isometric rear view, partially broken away, of the apparatus of FIG. 1 (after removal of the cover shown in FIG. 1)
Figure 3:
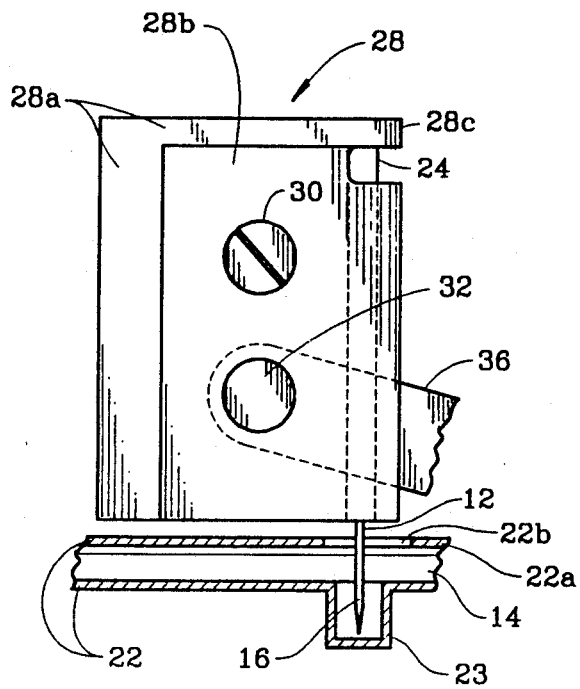
FIG. 3 shows an enlarged front view, partially broken away and sectioned, of inoculation needles and adjacent members of the apparatus, while the needles are immersed in serum.
Figure 4:
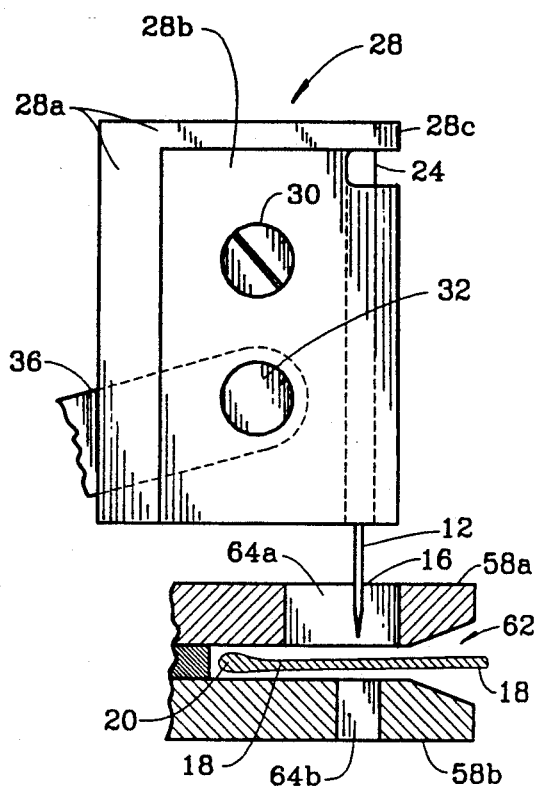
FIG. 4 corresponds to FIG. 3 but shows the needles in their starting position before inoculating the web of a chicken wing.
Figure 5:
FIG. 5 and 6 show side and front views of the inoculation needles and their handle.
Figure 6:
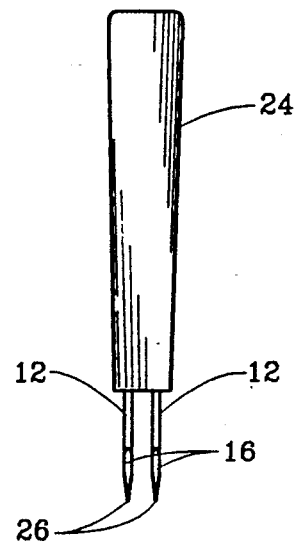
Figure 7:
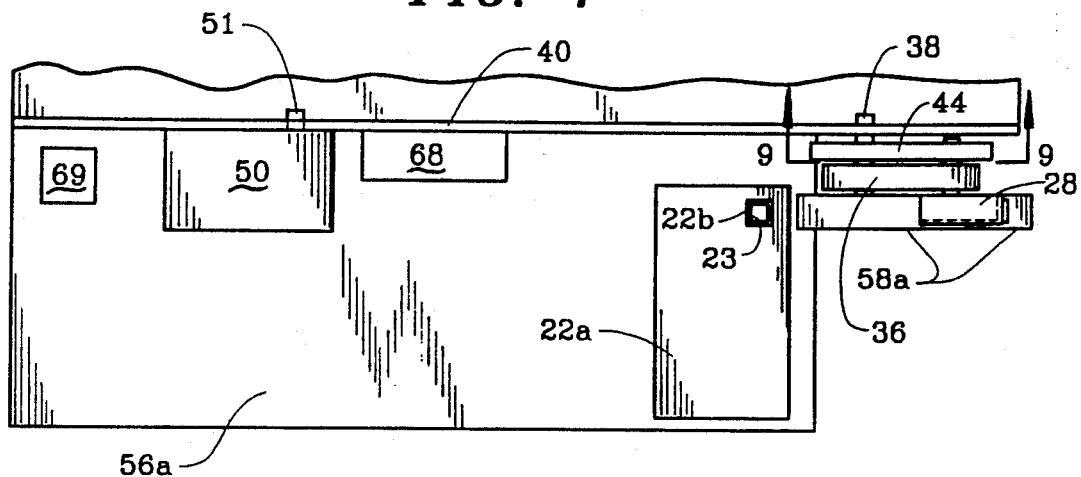
FIG. 7 shows and enlarged schematic and partially broken away top view of the apparatus shown in FIG. 1, (including a circuit interrupt omitted in FIG. 1), with revisions of those proportions exaggerated for illustrative purposes in FIG. 1.
Figure 8:
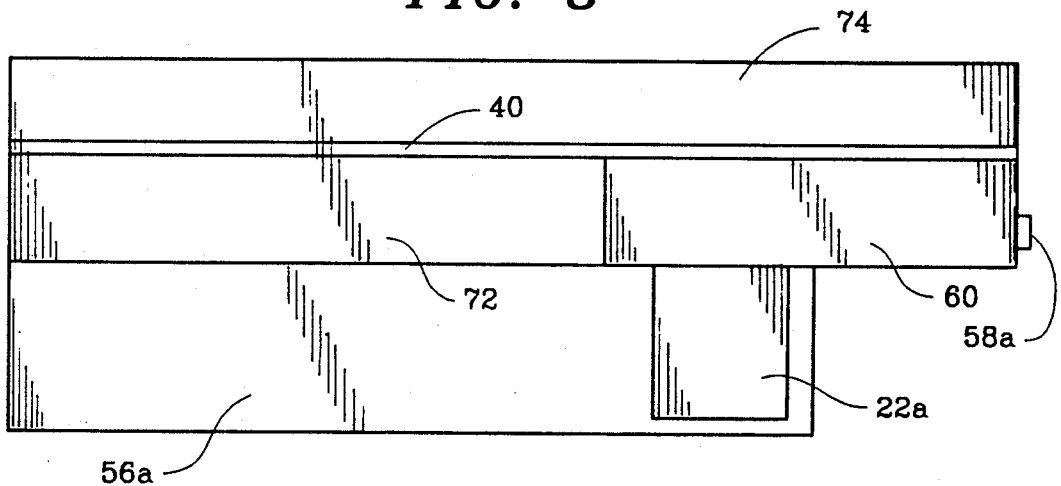
FIG. 8 shows a view corresponding to FIG. 7 but showing the whole top view after protective covers have been put in place.
Figure 9:
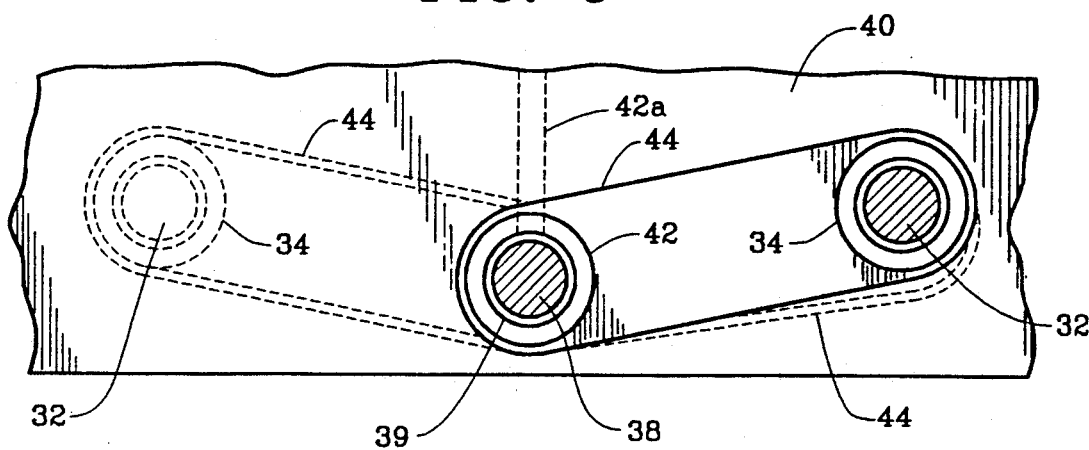
FIG. 9 shows an enlarged section taken on the line IX-IX shown in FIG. 7 (showing a belt trained around gears for holding the needles constantly vertical as they are moved, in full lines to show the belt position at the starting position of the needles shown in FIG. 4, and in dotted lines to show the belt positions at the end of downward movement from starting position and when the needles are fully immersed as shown in FIG. 3).

Referring now to the drawings, there is shown apparatus 10 for automatically causing a pair of injection needles 12, after each needle has received liquid serum 14 in a groove 16 along its side, to move toward and through the web 18 of a chicken's wing 20, and then to retract from the web and move across to, into and out of a serum reservoir 22 and its connecting well 23 beneath, and finally back to the starting position.

The pair of needles 12 are preferably the same as those conventionally used for manual inoculation of chicken wings. Their grooves 16 deposit serum in a wing web in essentially the same way that they do in perfectly executed manual operation of the needles, but with greater reliability, convenience, economy and safety. The indentations of grooves 16 may extend entirely through the needles instead of only partially as shown.

Needles 12 have their shank ends embedded in a conventional plastic handle 24. Their exposed ends are spaced apart and parallel. Their grooves 16 extend from close to their pointed ends 26 to about half way to the handle 24 and are adapted to retain enough serum for inoculating a wing as the needles move from the reservoir 22 and well 23 to the starting position, pause there for a period not long enough for significant evaporation, and then move to inoculate a wing web.

Needle handle 24 is held in a needle holder 28 having a main body 28a and a piece 28b releasably secured to the body 28a by a cap screw 30. Handle 24 is oriented vertically, with the needles extending down, and is pressed upwardly against a projection 28c from the top of body 28a. A grooved portion of piece 28b is then moved against one side of handle 24 while the other side of the handle is consequently pressed against a grooved portion of body 28a. Cap screw 30 is then tightened to lock 28b against 28a and thereby lock handle 24 in needle holder 28.

A shaft 32 has one end fixed to needle holder 28 and its other end fixed to a gear 34. The central part of shaft 38 is carried by and rotatable in one end of an arm 36. The other end of arm 36 is keyed to a shaft 38 extending through and journaled in a vertical support plate 40, for purposes of transmitting a rocking motion from shaft 38 to arm 36. Shaft 38 extends slidably through a plastic bushing 39. The outside of bushing 39 fits through a central opening through a gear 42 and through an integral extension of gear 42 which fits in an opening through plate 40 and is fixed to plate 40 by a set screw 42a extending down through plate 40 from its top edge. A shoulder around the outer end of bushing 39 prevents arm 36 from rubbing against gear 42 when arm 3b is rocked by shaft 38. Gear 42 is thus held stationary and concentric with shaft 38. A timer belt 44 is trained around gears 34 and 42 for purposes of controlling the orientation of needle holder 28 so that needles 12 will continue to extend vertically downward throughout movement of holder 38 as arm 36 swings in response to shaft 38.

Considering the needle side of plate 40 to be the front side, and the other side of plate 40 to be the back side, the end of rocking shaft 38 projecting from the back side of plate 40 is keyed to a pinion 46 driven by a rack 48, preferably in the form of a helically threaded bar. Movement of rack 48 is guided by pinion 46 and rollers 47. An electric motor 50 is secured to the front side of plate side 40 and has a drive shaft 51 extending through plate 40 and keyed to a crank arm 52 on the back side of plate 40. A connecting rod 54 is connected at its opposite ends to crank arm 52 and rack 48, so that rotation of motor 50 will cause endwise reciprocation of rack 48 far enough to rock pinion 46 through a predetermined arc and thereby cause arm 36 to swing needles 12 through the desired operating cycle.

Motor 50 is preferably of the kind exemplified by the subfractional (1/100 HP) AC gear motors supplied by W. W. Grainger, Inc. of Chicago, Ill., having a magnetically operated pawl to positively stop the motor shaft when the stop switch of the motor is operated. This insures that successive sequences of operation will stop and start at the same position of needle holder 28. The motor drive shaft has a projecting end on the front side of plate 40, for carrying a cooling fan (preferably used but not shown).

Plate 40 rests on and is secured to a horizontal base member 56, preferably of sheet metal and having a rectangular top 56a and four turned down rectangular sides 56b. One end of base 56 is shortened so that needles 12 are beyond base 56 when web injection occurs. A pair of parallel guard members 58a and 58b are fixed to and extend from that end of the base to keep fingers away from the needle points in their starting position and during their movement below that position during injection. A cover guard 60 is detachably secured to plate 40 to cover the needle holder 28 at its starting position and during injection. The bottom of guard 60 extends down to the level of the top of upper guard member 58a, which it largely covers.

Guards 58a-b are mounted one above the other with a slot 62 between them wide enough to receive a chicken wing inserted leading edge first, while the bird is held inverted with its head extending adjacent to cover guard 60. A cart (not shown) is conventionally used in connection with such chicken injections, and a supplemental support (not shown) is preferably connected between cart and base 56 to raise apparatus 10 to a convenient level and permit it to swivel around a vertical axis as may be convenient.

A start button 66 to operate a starting switch for motor 50 is mounted on a projection from base 56, near enough to slot 62 for an operator's hand to position a wing web into the slot and then use the wing to press the starting button.

The upper and lower guard members 58a and -b have vertical openings 64a and 64b through them to allow needles 12 to pass through during inoculation. The opening 64a through 58a is larger than opening 64b through 58b in order to increase the area of view through opening 58a of the top of a wing web being treated, while also reducing the area of opening 58b in order to increase the area of support of the web by the lower guard member 58b.

After motor 50 starts, it swings arm 36 to move needles 12 downwardly until their serum-carrying grooves 16 have entirely gone through web 18, then back to move needles 12 in a continuous swinging movement which first retracts the needles from web 18 and then carries them in a wide arc across to serum reservoir container 22 and well 23, which are mounted in a opening through the top of base 56 on the front side of plate 40. Well 23 is deep enough to entirely submerge grooves 16 in the well when the pointed needle ends stop just short of the bottom of the well at the end of the swinging movement of the needles into the reservoir.

At that stage the ungrooved exposed portions of the needles are submerged in the reservoir when it is full but not when its level of serum drops to the top of well 23. No significant amount of serum clings to the ungrooved sides of the needles, so changes in the level of serum in the reservoir 22 above well 23 do not affect the amount of serum picked up by the needles during each immersion. Well 23 controls what is supplied to needles and they continue to received the same amount of serum as long well 23 remains full. Well 23 has a much smaller cross-sectional area along its vertical length, and a much smaller liquid holding capacity, than the part of the container 22 above well 23.

The cover 22a across the top of the reservoir 22 is preferably of clear "Lexan" plastic or the like, to facilitate periodic inspection of how much serum is left in the reservoir. The capacity of the reservoir 22 above well 23 is preferably at least about 10 cc, which should be enough to inoculate at least 1000 chickens. The cover 22a has a small opening 22b through it to allow the needles 12 to pass into and out of reservoir 22 and well 23.

As soon as needle grooves 16 have been immersed in serum well 23, arm 36 reverses its swinging movement and swings back to the starting position of the cycle, where a micro-switch control button 70 is engaged and operated by a rear extension of crank arm 52 to stop motor 50 and automatically prevent further rotation of its drive shaft 51. Apparatus 10 is then ready for a new cycle as soon as start button 66 is pressed again.

A panel 68 is attached to the top of plate 40 to support a resetable counter 68*a* to show the number of cycles of operation since the last reset, a fuse 68*b*, a signal light 68*c* to show when power is on, and an on/off power switch 68*d*.

A ground fault interrupt 69 is mounted on base 56 to detect and prevent short circuits.

A guard cover 72 is detachably connected to plate 40, in order to cover the part of the apparatus on the front side of plate 40 which is not covered by cover 60, except for leaving enough of the transparent reservoir cover 22*a* exposed to permit inspection of how much serum is left in the reservoir. A cover 74 is also detachably connected to plate 40, to cover the drive mechanism on the back side of plate 40.

While a present preferred embodiment of the invention has been illustrated and described, it will be understood that the invention is not limited thereto but rather by the scope of the following claims.

I claim:

1. Apparatus for inoculating poultry, comprising an inoculation needle indented to retain serum applied to the needle and pointed at one end for piercing a web of a bird's wing; a container for liquid serum to be applied to the needle; means to position a bird's wing so that the web of the wing is positioned for injection by the needle; means mounting the wing positioning means and the container in laterally spaced positions, which locate the container where it is not entered by the needle when the needle extends through the web of a wing in the wing positioning means; means to move the needle, said moving means including needle holding means secured to the needle, movable means supporting the needle holding means, and the drive means connected to the movable means and operable to move the needle holding means back and forth along a fixed path having one end extending downwardly toward the container and its other end extending downwardly toward the position of the web of a wing in the wing positioning means; and means to direct the pointed end of the needle downward to enter the container when said needle holding means moves downwardly along said one end of its path, and to direct the pointed end of the needle downward to pass through where the web of a wing is positioned in the wing positioning means when the needle holding means moves downwardly along said other end of its path; means to actuate said directing means in response to movement of said movable means, whereby the drive means causes the needle to move down into and up out of the container and thereafter down and up through the web in the wing positioning means.

2. Apparatus according to claim 1, in which said path has a midway point which is between the container and the wing positioning means.

3. Apparatus according to claim 2, in which said directing means comprises a stationary gear adjacent said point, a gear fixed to the needle holding means, and a belt having teeth meshing with said gears.

4. Apparatus according to claim 1, comprising a motor connected to said drive means, and means to stop and start the motor where the needle is above the position of the web of a wing in the wing positioning means.

5. Apparatus according to claim 1, in which the serum container has an upper portion of relatively large capacity, and a lower portion of substantially less capacity below and opening into the upper portion, the lower portion forming a well deep enough to receive the indented portion of the needle.

6. Apparatus which according to claim 1, in which the wing positioning means comprises a member closely overlying the web of a wing when positioned in the wing positioning means, said member having an opening through it to allow the needle to move down to pass through the web, said opening being large enough to permit viewing through it from above, thereby facilitating observation and hence avoidance of any feather in the way of the needle which might wipe off serum on the needle before it injects a web.

7. Apparatus for innoculating poultry comprising an inoculation needle indented to retain serum applied to the needle and pointed at one end for piercing the web of a bird's wing; a container for liquid serum to be applied to the needle, means to position a bird's wing so that the web of the wing is positioned for injection by the needle; means mounting the wing positioning means and the container in laterally spaced positions which locate the container where it is not entered by the needle when the needle extends through the web of a wing in the wing positioning means; and arm; means connected to one end of the arm and supporting the arm for pivotal movement about said one end, said one end of the arm being positioned about midway between the container and the wing positioning means; means secured to the needle to hold the needle; means journaling the needle holding means on the other end of the arm; means to rock the arm about its said one end between a first position where it supports the needle holding means over the container and a second position where it supports the needle holding means over the wing positioning means; and means to direct the pointed end of the needle downwardly to enter the container when the arm is in the said first position, and to direct the needle downwardly to pass through the web of a wing in the wing positioning means when the arm is in its said second position.

8. Apparatus according to claim 7, in which the directing means comprises a stationary gear concentric with said means pivotally supporting said one end of the arm, a gear pivotally connected to the other end of the arm and secured to the needle holding means, and means meshing with said gears to cause the gear at said other end of the arm to turn enough when the arm rocks to constantly hold the needle substantially vertical.

9. Apparatus according to claim 8, in which the means meshing with the gears is a flexible belt trained around the gears and having teeth around its interior periphery which mesh with the gears.

10. Apparatus according to claim 7, in which said means pivotally supporting said one end of the arm is a rotatable shaft; and comprising means securing the rotatable shaft to the arm; a motor; a motor shaft; a crank fixed to the motor shaft; a drive member reciprocable lengthwise; means meshing together said drive member and rotatable shaft to cause the arm to rock back and forth once during each endwise reciprocation of said drive member; and means linking the crank and said drive member to cause the arm to rock back and forth once during each revolution of the motor shaft.

11. Apparatus according to claim 10 comprising a button positioned near the wing positioning means and manually operable to start the motor, means to stop the motor, means to detect when the needle completes its movement from the serum container to said second positions above the wing positioning means, and means operable by the detecting means to actuate the motor stopping means when the needle has moved to said second position.

12. Apparatus for inoculating poultry, comprising a container for serum, means for positioning a bird's wing with its web extending substantially horizontally, said wing positioning means comprising means to position horizontally the web of a wing in the wing positioning means, said web positioning means having an opening therethrough to permit a needle to move down through the opening to pierce a web extending across the opening, the container and the web positioning means being spaced laterally apart so that a needle extending through the opening cannot enter the container, means adapted to be secured to an inoculation needle to hold the needle, and means to move the needle holding means downwardly from a position above the web positioning means and thereby cause a needle held by the needle holding means to pass through said opening, to move the needle holding means up to withdraw a needle held by it from said opening, to move the needle holding means to a position above the container, to move the needle holding means downwardly toward and upwardly from the container for applying serum to the needle, and to move the needle holding means to return it to its said position above the web positioning means, said means for moving the needle holding means comprising a supporting structure, mounting means fixed to said structure, means pivotable about said fixed mounting means, means mounting the needle holding means to pivot on the pivotable means, and means to cause the needle holding means to pivot on the pivotable means to maintain constant orientation of the needle holding means during movement of the pivotable means about its fixed pivotal mounting means, whereby a needle held downwardly by the needle holding means is caused to continue to project downwardly during movement of the pivotable means about its fixed mounting means.

13. Apparatus according to claim 25, in which said means to cause the needle holding means to maintain constant orientation comprises a gear secured to the needle holding means, a second gear, and a belt trained around said gears.

* * * * *